United States Patent [19]

Scher et al.

[11] Patent Number: 4,994,261

[45] Date of Patent: Feb. 19, 1991

[54] PESTICIDE COMPOSITIONS AND METHOD

[75] Inventors: Herbert B. Scher, Moraga; Marius Rodson, El Cerrito; Ronald L. Morgan, Daly City, all of Calif.

[73] Assignee: ICI Americas Inc., Wilmington, Del.

[21] Appl. No.: 232,193

[22] Filed: Aug. 15, 1988

Related U.S. Application Data

[63] Continuation of Ser. No. 846,183, Mar. 31, 1986, abandoned.

[51] Int. Cl.$^5$ .............................................. A01N 57/18
[52] U.S. Cl. .................................... 424/10; 514/141; 514/974
[58] Field of Search .................. 424/10; 514/141, 974

[56] References Cited

U.S. PATENT DOCUMENTS

| 2,988,474 | 6/1961 | Szabo et al. | 514/141 |
| 3,959,464 | 5/1976 | DeSavigny | 424/78 |
| 4,140,516 | 2/1979 | Scher | 71/88 |
| 4,285,720 | 8/1981 | Scher | 71/88 |

FOREIGN PATENT DOCUMENTS

0134674 9/1988 European Pat. Off. ............ 514/141

*Primary Examiner*—Allen J. Robinson
*Attorney, Agent, or Firm*—Denis A. Polyn

[57] ABSTRACT

Toxicant, especially pesticide compositions, having lowered dermal toxicity are provided. The compositions include a lipophilic-pesticide, a nonionic surfactant and a dry inert diluent carrier. Methods for reducing the dermal toxicity of lipophilic toxicants, especially pesticides are provided, as well as methods for controlling insect pests using the disclosed compositions.

12 Claims, No Drawings

PESTICIDE COMPOSITIONS AND METHOD

This is a continuation of application Ser. No. 846,183, filed Mar. 31, 1986, now abandoned.

FIELD OF THE INVENTION

The invention relates to dermally toxic pesticide compositions consisting of the pesticide and a dry, inert diluent carrier, that have been additionally safened for handling by addition thereto of a nonionic surfactant having an HLB of from about 17 to about 20.

BACKGROUND OF THE INVENTION

A wide variety of pesticides are commonly used in agronomic and horticultural pursuits. As used herein the term "pesticide" means any chemical compound or composition which displays biological activity in an agricultural field site or at any locus where control of biological growth is desired. The biological activity or control contemplated herein includes all forms of growth modification, ranging from regulation and retardation to killing, and extends to all forms of plant and animal life found in an agricultural environment during some time during the pest's life cycle. Pesticides within this invention include anti-foulants, plant growth regulants, soil fumigants, molluscicides, insecticides, herbicides, fungicides, rodenticides, nematocides, algicides, predator control agents, and insect and animal repellents. Additional biologically active compounds can also be present in admixture with the primary ingredient, such as synergists, antidotes, fertilizers, soil life extenders, and additional pesticides.

The term "biologically effective amount" is used herein to denote any quantity of pesticide or pesticide composition, which when applied to an agricultural site in any conventional manner causes the occurrence of one or more of the biological effects mentioned above. As further explained in the latter portion of this specification, the quantity of pesticide applied in a given situation depend on the pesticide itself, on the type of biological activity inherent in the pesticide, and the degree of such activity sought to be achieved. The selection of the proper quantity to be applied, however, is within the expertise of one skilled in the art.

Some pesticides, such as the chlorinated hydrocarbon carbamate insecticides and the organophosphorus pesticide compounds, including phosphonate, organophosphate and organothiophosphate compounds present a problem of dermal toxicity to persons handling these substances.

If handled carelessly, improperly or in disregard of directions, the pesticide, depending upon its toxicity, may present a hazard to those handling the pesticide whether in packaging it for sale, handling it for shipment, mixing it for field application or applying it in the field. The toxicity of the pesticide will vary depending upon a number of factors, including the inherent toxicity of the pesticide substance at its site of biological action. Various physical properties of the pesticide including the hydrophilic-lipophilic balance of the pesticide affect the adsorption to and absorption by various tissues of the person handling the pesticide compound, and thus affect the toxicity of the compound to the person handling it.

Thus, it is desirable to develop formulations for these pesticide compounds that reduce the dermal toxicity of the compounds to persons handling them yet still preserve the pesticidal effectiveness of the compounds as applied to the pest or the locus where the pest may be found.

SUMMARY OF THE INVENTION

There has now been discovered a pesticidal composition that maintains high biological effectiveness against pests when used in the field and has reduced dermal toxicity.

The compositions comprise a biologically effective amount of a dermally toxic pesticide, a nonionic surfactant having an HLB of from about 17 to about 20 and a dry inert diluent carrier.

More particularly, the compositions comprise (a) a biologically effective amount of a dermally toxic pesticide;

(b) a dinonyl phenol ethoxylate surfactant; and (c) a dry inert diluent clay carrier, in granular form.

Dermal toxicity includes systemic toxic effects that occur in an animal or human as a result of dermal contact with a toxic substance for a defined period of time. Dermal toxicity may be defined as the LD-50 (lethal dose to 50% of the animals in a test group) caused by a 24 hour exposure to a toxic substance.

Pesticides of the composition disclosed herein include dermally toxic organophosphorus, pyrethroids, phosphonate and thiophosphonate compounds. The following are examples of such compounds, followed in parenthesis by their common names, where available:

S-tert-butylthiomethyl O,O-diethyl phosphorodithioate (terbufos)

O,O-diethyl-O-4-methylsulphinylphenyl phosphorothioate (fensulfothion)

O,O-diethyl O-2-isopropyl-6-methylpyridimidin-4-yl phosphorothioate (diazinon)

O,O-diethyl S-2-ethylthioethyl phosphorodithioate (disulfoton)

S-chloromethyl O,O-diethyl phosphorodithioate (chlormephos)

O-ethyl S,S-dipropyl phosphorodithioate (ethoprophos)

O,O-diethyl S-ethylthiomethyl phosphorodithioate (phorate)

O-(4-bromo-2-chlorophenyl) O-ethyl S-propyl phosphorodithioate (prophenofos)

S-1,2-di(ethoxycarbonyl)ethyl O,O-dimethyl phosphorodithioate (malathion)

O,O,O',O'-tetraethyl S,S''-methylene di(phosphorodithioate) (ethion)

O-(4-bromo-2,5-dichlorophenyl) O,O-diethyl phosphorothioate (bromophos-ethyl)

S-4-chlorophenylthiomethyl O,O-diethyl phosphorodithioate (carbophenothion)

2-chloro-1-(2,4-dichlorophenyl)vinyl diethyl phosphate (chlorphenvinphos)

O-2,5-dichloro-4-(methylthio) phenyl O,O-diethyl phosphorodithioate (chlorthiophos)

O-4-cyanophenyl O,O-dimethyl phosphorothioate (cyanophos)

O,O-dimethyl O-2-methylthioethyl phosphorothioate (demiphion)

O,O-diethyl O-2-ethylthioethyl phosphorothioate (demeton)

O-2,4-dichlorophenyl O,O-diethyl phosphorothioate (dichlorofenthion)

O-2,4-dichlorophenyl O-ethyl phenylphosphonothioate (EPBP)

O,O-diethyl O-5-phenylisoxazol-3-yl phosphorothioate (isoxathion)
1,3-di(methoxycarbonyl)-1-propen-2-yl dimethyl phosphate
1,4-dioxan-2,3-diyl S,S-di(o,O-diethyl phosphorothioate (dioxathion)
O,O-dimethyl-O-4-nitro-m-tolyl phosphorothioate (fenitrothion)
O,O-dimethyl O-4-methylthio-m-tolyl phosphorothioate (fenthion)
O-(5-chloro-1-isopropyl-1,2,4-triazol-3-yl) O,O-diethyl phosphorothioate (isazophos)
S-2-isopropylthioethyl O,O-dimethyl phosphorodithioate (isothioate)
4-(methylthio)phenyl dipropyl phosphate (propaphos)
1,2-dibromo-2,2-dichloroethyl dimethyl phosphate (naled)
O,O-diethyl α-cyanobenzylideneamino-oxyphosphonothioate (phoxim)
O,O-diethyl O-4-nitrophenyl phosphorothioate (parathion)
O-2-diethylamino-6-methylpyrimidin-4-yl O,O-diethyl phosphorothioate (pirimiphos-ethyl)
O-2-diethylamino-6-methylpyrimidin-4-yl O,O-dimethyl phosphorothioate (pirimiphos-methyl)
O,O,O',O'-tetraethyldithiopyrophosphate (sulfotep)
O,O,O',O'-tetramethyl O,O'-thiodi-p-phenylene diphosphorothioate (temephos)
S-2-ethylthioethyl O,O-dimethyl phosphorodithioate (thiometon)
O,O-diethyl O-1-phenyl-1,2,4-triazol-3-yl phosphorothioate (triazophos)
O-ethyl O-2,4,5-trichlorophenyl ethylphosphonothioate (trichloronate)
(±)-3-allyl-2-methyl-4-oxocyclopent-2-enyl (±)-cis,-trans-chrysanthemate (allethrin)
(±)-3-allyl-2-methyl-4-oxocyclopent-2-enyl (±)-trans-chrysanthemate (bioallethrin)
3-phenoxybenzyl (±)-cis,trans-chrysanthemate (phenothrin)
pyrethrins
2-(2-butoxyethoxy)ethyl thiocyanate
isobornyl thiocyanoacetate (terpinyl thiocyanoacetate)
carbon disulfide
2-(4-tert-butylphenoxy)cyclohexyl prop-2-ynyl sulphite (propargite)
4,6-dinitro-6-octylphenyl crotonates (dinocap)
ethyl 4,4'-dichlorobenzilate (chlorobenzilate)
S,S,S-tributyl phosphorotrithioate
tributyl phosphorotrithioite (merphos)
copper naphthenates
5-ethoxy-3-trichloromethyl-1,2,4-thiadiazole (etridiazole)
O-ethyl S,S-diphenyl phosphorodithioate (edifenphos)
6-butoxycarbonyl-2,3-dihydro-2,2-dimethylpyran-4-one (butopyronoxyl)
N,N-diethyl-m-toluamide (deet)
dibutyl phthalate
dibutyl succinate
1,5a,6,9,9a,9b-hexahydro-4a(4H)-dibenzofurancarboxaldehyde
dipropyl pyridine-2,5-dicarboxylate Of the many different types of pesticides useful in the present composition, certain classes are preferred. One preferred class is that of organophosphorus compounds, particularly those of the formula:

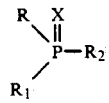

in which X is oxygen or sulfur; and R, $R_1$ and $R_2$ are independently selected from the group consisting of $C_1$–$C_6$ alkyl, $C_1$–$C_6$ alkoxy, $C_1$–$C_6$ alkylthio, $C_2$–$C_6$ alkenyl, $C_2$–$C_6$ alkenoxy, $C_2$–$C_6$ alkenylthio, phenyl, phenoxy, phenylthio, $C_7$–$C_9$ phenylalkyl, $C_7$–$C_9$ phenylalkoxy, and $C_7$–$C_9$ phenylalkylthio, each member of such group optionally substituted with up to three substituents selected from halogen, $C_1$–$C_4$ alkyl, $C_1$–$C_4$ alkoxy, cyano, and nitro.

The terms "alkyl," "alkoxy," etc., are intended to include both straight-chain and branched-chain groups, and all carbon atoms ranges are inclusive. More preferred organophosphorus compounds are those in which X is sulfur, and R, $R_1$ and $R_2$ are independently $C_1$–$C_4$ alkoxy or phenoxy, the phenyl ring optionally substituted with up to three groups selected from $C_1$–$C_3$ alkyl, nitro, cyano, and halogen. Highly preferred are those in which X is sulfur, R is $C_1$–$C_4$ alkoxy, $R_1$ is $C_1$–$C_4$ alkoxy, and $R_2$ is phenoxy substituted with up to three substituents selected from $C_1$–$C_3$ alkyl and nitro.

Specific preferred pesticide compounds include S-tert-butylthiomethyl-O,O-diethylphosphorodithioate and O,O-diethyl-S-ethylthiomethylphosphorothioate.

The most highly preferred are compounds of the general formula:

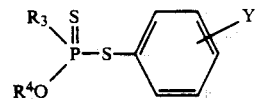

wherein $R_3$ and $R_4$ are selected from the group consisting of methyl and ethyl and Y is selected from the group consisting of hydrogen and alkyl groups having up to 4 carbon atoms.

The most highly preferred pesticide compounds serving as the active ingredients in the compositions of this invention are those described in U.S. Pat. No. 2,988,474, with the most preferred compound being o-ethyl-S-phenylethyl phosphonodithioate, sold under the tradename Dyfonate ® by Stauffer Chemical Company.

Surfactants which are suitable for use in the compositions are nonionic and have an HLB (hydrophilic-lipophilic balance) of from about 17 to about 20.

The most preferred surfactant is manufactured under the tradename Igepal ® DM 970 by the GAF Corporation, and under different tradenames by various companies, and is a dinonyl phenyl-150 mole ethoxylate. It has an HLB of 19.0.

The inclusion of the nonionic surfactant in this formulation serves to chemically stablize the organophosphorus or other active pesticide compound on the clay granules, and also has the effect of reducing the dermal toxicity of the organophosphorus/clay granule formulation.

Other suitable surfactants of the general composition are, for example, alkyl and dialkylphenoxy poly(ethyleneoxy) ethanols. Suitable surfactants of the above-mentioned HLB range are exemplified by surfactants of the following structural formula

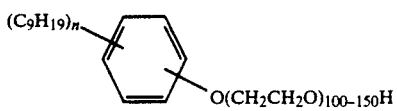

wherein n is 1 or 2.

Further examples of appropriate surfactants according to the invention are summarized in Table I.

TABLE I

| HLB | Commercial Name | Structure |
|---|---|---|
| 17.9 | Myrj 53 | polyoxyethylene (50) stearate |
| 18.0 | Etocas 100 | ethoxylated (100) castor oil |
| 18.0 | Lantrol AWS | alkoxylated lanolin oil |
| 18.0 | Veronic L167 | ethoxylated coco mono-glyceride |
| 18.1 | Alcasurf CO200 | ethoxylated castor oil |
| 18.1 | Chemmax CO-200/50 | ethoxylated castor oil |
| 18.1 | Pegosperse CO200 | POE 200, castor oil |
| 18.1 | Veronic Li48 | ethoxylated mono and diglyceride |
| 18.0 | Tergitol 15-S-50 | secondary alcohol PEG ether |
| 18.3 | Kessco polyethylene glycol | esters, PEG 4000 monoleate |
| 18.8 | Brig 700 | polyethylene 100 stearyl ether |
| 18.8 | Kessco PEG esters | PEG monostearate |
| 18.5 | Pluronic L-35 | |
| 17.0 | Pluronic P-65 | |

Preferred clays for use as the inert diluents in the compositions of this invention are those from the attapulgite group and those from the montmorillonoid group. The attapulgite clays have the prototype formula $Mg_5Si_8O_{20}(OH)_{28}H_2O$ and those of the montmorillonoid group have the prototype formula $Al_2(Si_4O_{10})(OH)_2$.

The attapulgite clays are most effective for use in the compositions of the invention as inert diluent carriers.

Both of these types of clays are well known to those skilled in the art and are described in the *Handbook of Insecticide Dust Diluents and Carriers*, by T.C. Watkins and L.B. Norton, Dorland Books, Caldwell, N.J. (1955).

Other conventional diluent carriers can be used, but the clays are preferable.

The active ingredients (pesticide and surfactant) are sprayed onto the clays and blended to yield formulations with the active component distributed uniformly throughout the mass. The granular compositions of this invention are most useful in a size range of from 10–60, preferably 18–48 mesh, U.S. Sieve Series Number.

Accordingly, the preferred composition of this invention comprises (a) from about 1 to about 45 percent by weight of a biologically effective amount of an organophosphorus compound of the formula

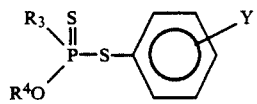

wherein $R_3$ and $R_4$ are selected from the group consisting of methyl and ethyl and Y is selected from the group consisting of hydrogen and alkyl groups having up to 4 carbon atoms.

(b) from about 0.1 to about 10 percent by weight of dinonyl phenol 150 mole ethoxylate; and (c) from about 50 to about 98 percent by weight clay granules.

While the formulation set forth above is described in terms of an organophosphorus compound such as described in U.S. Pat. No. 2,988,474, it is also contemplated that other hydrophobic pesticides—clay granule formulations can be dermally safened using this class of surfactants as described herein.

Formulations of the type described herein are set forth below.

| Counter ®* | 15% | Thimet ®** | 20% |
|---|---|---|---|
| attapulgite clay granules | 80% | attapulgite clay granules | 75% |
| Igepal DM 970 | 5% | Igepal DM 970 | 5% |
| | 100% | | 100% |
| Dyfonate ® | 15% | Dyfonate ® | 20% |
| attapulgite clay granules | 80% | attapulgite clay granules | 75% |
| Igepal DM 970 | 5% | Igepal DM 970 | 5% |
| | 100% | | 100% |

*= S-tert-butylthiomethyl O,O-diethyl phosphorodithioate
**= O,O-diethyl S-ethylthiomethylphosphorodithioate The Igepal DM970 has the structural formula

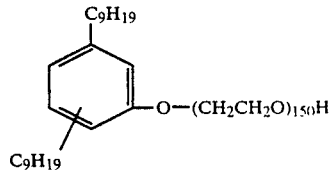

The pesticide formulation is normally prepared by taking a quantity of Dyfonate ® and mixing therewith the desired quantity of Igepal DM 970 and applying that mixture to clay granules, and mixing the clay granules with the active ingredient thoroughly. A typical process is as follows.

EXAMPLE 1

Five grams (5 g) of Igepal DM970 was dissolved in a solution of 15.82 g of Dyfonate ® technical material (95% active ingredient) in a water bath heated between 55°–75° C. This solution was then added with a pipette to a quantity (79.18 g) of clay granules in a rotating beaker. The tumbling was continued for approximately one hour after the addition of the active ingredient to effect mixing of all of the components.

The pesticide compositions according to the invention may have various amounts of pesticide, surfactant and dry inert diluent carrier.

The amount of pesticide compound included in the pesticidal granule composition depends on the absorption capacity of the inert carrier and the spreading efficacy of the application equipment. In general, the pesticide may comprise from 1% to about 45% of the composition on a weight basis, preferably about 15%.

Expressed as a weight percent of the whole composition, the surfactant may range between about 0.1% and about 10% with a preferred range of between 1% and 6% and an optimal range of between 2% and 5%, depending upon the exact composition of the surfactant.

The amount of dry inert diluent carrier in pesticidal compositions may vary between 50% and about 98%, most preferably about 80%.

The invention will be better understood with respect to the following examples which are intended by the inventors to be exemplary only and non-limiting.

The reduction in dermal toxicity achieved by the use of the compositions of the invention is demonstrated in accordance with the following examples.

In conducting the dermal toxicity tests in Example II, a comparison was made between two formulations: one of these formulations containing the Igepal DM 970 nonionic surfactant, and the other containing a conventional chemical stabilizer, dipropylene glycol. The dermal toxicity was measured in accordance with the following technique.

EXAMPLE II

Dermal Toxicity

Acute dermal toxicity was determined in accordance with the Environmental Protection Agency's Proposed Guidelines for Registering Pesticides in the U.S.; Hazard Evaluation: Humans and Domestic Animals, *Fed. Reg.* 43:163, 37336-37402 (Aug. 22, 1978).

Albino rabbits (Stauffland White strain, Phillips Rabbitry, Soquel, Calif.) were housed in temperature controlled animal rooms (65°-70° F.), two to a cage in suspended steel cages (24"×16.5"×14"). Feed (Special Mixture, Gunter Bros., Morgan Hill, Calif.) and water were provided ad libitum.

Prior to treatment, the rabbits were randomly selected and individually identified using numbered ear tags. The day before treatment the skin areas to be treated were closely clipped and the rabbits were fasted overnight with water available.

The first dose tested was 501 mg/kg in 10 rabbits, 5 males and 5 females. Doses were thereafter selected at logarithmically spaced intervals. The levels selected produced at least three test groups with mortality rates between 10% and 90% and permitted calculation of the $LD_{50}$ (abraded skin and/or intact skin) of males and females with a 95% confidence interval of 20% or less. At least three dose levels and controls were tested.

Four male and four female rabbits were used for each succeeding dose level. In some of the tests, half of the rabbits at each dose level were further prepared by making epidermal abrasions with a needle in a crosshatch manner over the entire exposure area. The abrasions were sufficiently deep to penetrate the stratum corneum, but not the dermis. A single application of the composition was applied neat to the dose site. The composition was held in contact with the skin by a non-absorbent binder. To insure the integrity of the binder an outer wrapping of gauze was applied. At the end of the 24 hour exposure period, the wrappings were removed and the skin wiped and/or washed to remove any remaining test substance. The animals were then wrapped with fresh gauze which was left in place for 72 hours.

Four rabbits (two of each sex) were sham-treated by wrapping each in a similar manner.

Animals were observed for at least 14 days after dosing or until all signs of reversible toxicity in survivors subsided, whichever occurred later.

Observation for clinical signs and mortality were recorded frequently the first day, and early morning and late afternoon thereafter. The animals were observed once a day during weekends and holidays. All clinical signs were recorded for the onset, duration and severity. Rabbits were weighed on days 0 (prior to treatment), 7, 14 or at death, with the mean body weight calculated for each day.

The acute dermal toxicity in these tests was found to be unaffected by prior abrasion of the skin of the test animals. The results of these tests are reported in Table II.

TABLE II

Determination of $LD_{50}$ According to the Method of Litchfield and Wilcoxon
Route: Dermal   Species: Rabbit   Sex: Both

| | Formulation | Dermal $LD_{50}$ |
|---|---|---|
| 1. | 15% Dyfonate ®<br>5% dipropylene glycol<br>80% attapulgite clay granules<br>100% | 254 (163–394)* |
| 2. | 15% Dyfonate ®<br>5% Igepal DM 970<br>80% attapulgite clay granules<br>100% | 453 (307–667)* |

*Values in parentheses are 95% confidence limits.
$LD_{50}$ is measured in mg of composition per kg of body weight.

It can be seen by comparing the application of the two formulations above that the pesticide formulation containing the Dyfonate ®, Igepal DM 970 and attapulgite clay was about one-half as dermally toxic as was the comparison formulation containing Dyfonate ®, dipropylene glycol and attapulgite clay.

EXAMPLE III

Similar tests were conducted with additional formulations wherein the active ingredient was varied by replacing the Dyfonate ® pesticide with other pesticides of the organophosphorus-type. The results of these tests, along with the formulations, are set forth in Table III below.

TABLE III

Determination of $LD_{50}$ According to the Method of Litchfield and Wilcoxon
Route: Dermal   Species: Rabbit   Sex: Both

| | Formulation | Dermal $LD_{50}$ |
|---|---|---|
| 1. | 20% Thimet ®<br>5% dipropylene glycol<br>75% attapulgite clay<br>100% | 162 (136–182)* |
| 2. | 20% Thimet ®<br>5% Igepal DM 970<br>75% attapulgite clay<br>100% | 231 (208–258)* |
| 3. | 15% Counter ®<br>5% dipropylene glycol<br>80% attapulgite clay<br>100% | 23.5 (19.7–28.1) |
| 4. | 15% Counter ®<br>5% Igepal DM 970<br>80% attapulgite clay<br>100% | 42.9 (36.7–50.3) |

*Values in parentheses are 95% confidence limits.
$LD_{50}$ is measured in mg of composition per kg of body weight.

Again it will be seen that the substitution of the surfactant Igepal DM 970 for dipropylene glycol was effective in reducing the dermal toxicity of the formulation by a factor of about 2.

INSECTICIDAL EFFECTIVENESS

The insecticidal effectiveness of the composition was tested in the following manner:

One cubic centimeter (cc) of Western spotted cucumber beetle larvae (*Diabrotica undecimpunctata*) supplied by Mannerheim containing about 7,000 eggs was diluted to a final concentration of 250 eggs/cc by suspending 0.5 cc of undiluted eggs in 14 cc of water containing 0.2% Dacagin (Diamond Alkali Co.). Eggs may be stored in this suspension for 5 days at 5° C. without significant loss of viability.

Ten grams (10 g) of moist "Supersoil" (Wonderline, Rod McLellan Co., San Francisco, Calif.) were placed in a one ounce clear plastic cup (Thunderbird Container Corporation, El Paso, Tex.). The test material was dissolved in acetone or an appropriate solvent. A 0.05 milliliter (ml) aliquot of the test sample that had been diluted to the desired concentration was added to the soil. The cup was capped and the soil was mixed on a Vari-Whirl mixer for approximately 15 seconds. An indentation was made on the surface of the soil and 0.2 cc of the egg suspension was added. The eggs were covered with soil and maintained at room temperature (approximately 70° F). Four days later a section of Romaine lettuce leaf was placed in the treated cups. One week later the cups were examined for live larvae.

Test concentrations range from 10 ppm down to that at which approximately 50% mortality occurs.

There were two test compositions used to compare the insecticidal effectiveness of the compositions of this invention. The first composition (1) formulated in accordance with the compositions of the invention contained 15% Dyfonate ®, 5% Igepal EM 970 and 80% attapulgite, and the second (2) contained 20% Dyfonate ®, 5% dipropylene glycol and 75% attapulgite. The results of these tests are set forth in Table IV below.

TABLE IV

| | Diabrotica LC$_{50}$ Value (ppm) |
|---|---|
| Composition No. 1 | 0.4 |
| Composition No. 2 | 0.4 |

As can be seen from the results set forth above, the LC$_{50}$ value against Diabrotica of the composition of the invention was the same as that of a similar composition containing the conventional chemical stabilizer, dipropylene glycol. This demonstrates that the substitution of the Igepal DM 970 for dipropylene glycol does not adversely effect the biological effectiveness of the active ingredient.

It will be readily apparent to those skilled in the art that the compositions of the invention offer markedly reduced dermal toxicity without significantly reducing the biological effectiveness of the pesticidal compound used in the composition.

What is claimed is:

1. A granular organophosphorus pesticide composition that has been safened for handling comprising:
   (a) from about 1 to about 45 percent by weight of a biologically effective amount of a dermally toxic organophosphorus pesticide compound;
   (b) from about 0.1 to about 10 percent by weight of a nonionic surfactant of the formula

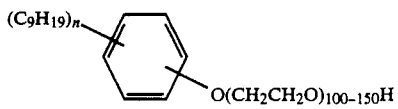

wherein n is 1 or 2; and
   (c) from about 50 to about 98 percent by weight of a dry inert diluent carrier.

2. The pesticide composition of claim 1 wherein said organophosphorus pesticide compound is selected from the group consisting of phosphonates and thiophosphonates.

3. The pesticide composition of claim 1 wherein said pesticide compound comprises those of the formula

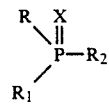

in which X is oxygen or sulfur; and R, R$_1$ and R$_2$ are independently selected from the group consisting of C$_1$–C$_6$ alkyl, C$_1$–C$_6$ alkoxy, C$_1$–C$_6$ alkylthio, C$_2$–C$_6$ alkenyl, C$_2$–C$_6$ alkenoxy, C$_2$–C$_6$ alkenylthio, phenyl, phenoxy, phenylthio, C$_7$–C$_9$ phenylalkyl, C$_7$–C$_9$ phenylalkoxy, and C$_7$–C$_9$ phenylalkylthio, wherein each member of such group optionally substituted with up to three substituents selected from halogen, C$_1$–C$_4$ alkyl, C$_1$–C$_4$ alkoxy, cyano, and nitro.

4. The pesticide composition of claim 2 wherein said organophosphorus pesticide compound comprises those of the formula

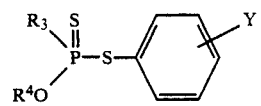

in which R$_3$ and R$_4$ are selected from the group consisting of methyl and ethyl and Y is selected from the group consisting of hydrogen and alkyl groups having up to 4 carbon atoms.

5. The composition of claim 1 wherein said surfactant is dinonyl phenol-150 mole ethoxylate.

6. The composition of claim 1 wherein said organophosphorus compound comprises about 15% on a weight basis of said composition.

7. The composition of claim 1 wherein the dry inert diluent carrier is an attapulgite clay and comprises at least about 50% on a weight basis of said composition.

8. The method of reducing dermal toxicity to a mammal exposed to a biologically effective amount of a granular, dermally toxic organophosphorus pesticide compound comprising the steps of adding to said dermally toxic organophosphorus compound an amount of a nonionic surfactant of the formula

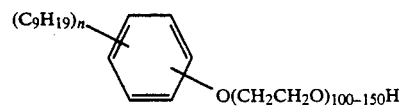

wherein n is 1 or 2 sufficient to reduce the dermal toxicity of said dermally toxic organophosphorus compound.

9. The method of claim 8 wherein said dermally toxic compound is O-ethyl-S-phenyl-ethyl phosphonodithioate.

10. The method of controlling an insect pest comprising applying to the locus where said insect pest is found during some part of its life cycle an insecticidally effective amount of a granular insecticidal composition comprising:
   (a) from about 1 to about 45 percent by weight of a biologically effective amount of an organophosphate compound having the formula

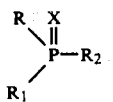

in which X is oxygen or sulfur; and R, $R_1$ and $R_2$ are independently selected from the group consisting of $C_1$–$C_6$ alkyl, $C_1$–$C_6$ alkoxy, $C_1$–$C_6$ alkylthio, $C_2$–$C_6$ alkenyl, $C_2$–$C_6$ alkenoxy, $C_2$–$C_6$ alkenylthio, phenyl, phenoxy, phenylthio, $C_7$–$C_9$ phenylalkyl, $C_7$–$C_9$ phenylalkoxy, and $C_7$–$C_9$ phenylalkylthio, each member of such group optionally substituted with up to three substituents selected from halogen, $C_1$–$C_4$ alkyl, $C_1$–$C_4$ alkoxy, cyano, and nitro;
(b) from about 0.1 to about 10 percent by weight of a dinonyl phenyl ethoxylate surfactant and
(c) from about 50 to about 98 percent by weight of a dry inert diluent carrier.

11. The method of claim 10 wherein said organophosphate compound is O-ethyl-S-phenyl-ethyl phosphonodithioate.

12. A granular organophosphorus pesticide composition that has been safened for handling comprising:
(a) from about 1 to about 45 percent by weight of a biologically effective amount of a dermally toxic O-ethyl-S-phenyl-ethyl-phosphonodithioate;
(b) from about 0.1 to about 10 percent by weight of a nonionic surfactant of the formula

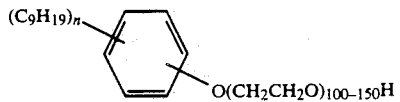

wherein n is 1 or 2; and
(c) from about 50 to about 98 percent by weight of a dry inert diluent carrier.

* * * * *